United States Patent
Witte

(10) Patent No.: US 6,418,348 B1
(45) Date of Patent: Jul. 9, 2002

(54) IMPLANTABLE LEAD WITH SELECTIVELY OPERABLE ELECTRODES

(75) Inventor: Joachim Witte, Berlin (DE)

(73) Assignee: Biotronik Mess-und Therapiegeraete GmbH & Co. Ingenieurbuero Berlin, Berlin (DE)

(*) Notice: Subject to any disclaimer, the term of this patent is extended or adjusted under 35 U.S.C. 154(b) by 0 days.

(21) Appl. No.: 09/599,936

(22) Filed: Jun. 22, 2000

(30) Foreign Application Priority Data

Jun. 25, 1999 (DE) .......................... 199 30 265

(51) Int. Cl.[7] .................................. A61N 1/05
(52) U.S. Cl. ..................... 607/122; 607/119
(58) Field of Search .................. 607/38, 66–67, 607/116, 119, 122–123, 115; 600/372–374, 377, 381

(56) References Cited

U.S. PATENT DOCUMENTS

| | | | |
|---|---|---|---|
| 4,484,352 A | 11/1984 | Katzin | 383/65 |
| 4,484,586 A | 11/1984 | McMickle et al. | |
| 4,628,934 A | 12/1986 | Pohndorf et al. | 128/419 |
| 4,848,352 A | 7/1989 | Pohndorf et al. | |
| 4,877,032 A * | 10/1989 | Heinze et al. | 607/2 |
| 5,336,253 A * | 8/1994 | Gordon et al. | 607/122 |
| 5,423,873 A * | 6/1995 | Neubauer et al. | 607/68 |
| 5,824,030 A | 10/1998 | Yang et al. | 607/122 |
| 5,968,086 A * | 10/1999 | Bonner et al. | 607/122 |

FOREIGN PATENT DOCUMENTS

| | | |
|---|---|---|
| DE | 693 21 030 | 5/1999 |
| EP | 0 571 797 | 12/1993 |
| WO | WO99/20340 | 4/1999 |

\* cited by examiner

Primary Examiner—Kennedy Schaetzle
Assistant Examiner—Kristen Droesch
(74) Attorney, Agent, or Firm—Venable; Robert Kinberg; Catherine M. Voorhees

(57) ABSTRACT

An implantable electrode arrangement which includes an electrode line (10) with a plurality of electrically conductive surface regions in the region of the distal end of the electrode line (10) for outputting electrical signals to a heart and/or for receiving signals from a heart, which can be connected by way of at least one electric line (18) of the electrode line (10) to a cardioelectric device such as a defibrillator or cardiac pacemaker, which device receives electrical signals and/or outputs pulses, wherein arranged in the electrode line (10) are switching means which are connected to the electric line (18) and at least one electrically conducting surface region and which are such that they can make or break a connection between the electrically conducting surface region and the cardioelectric device in the region of the electrode line (10), and arranged in the electrode line (10) are control means which are connected to the electric line (18) for receiving control signals and to the switching means for switching over from a state of the switching means of breaking the connection between the electric line (18) and the electrically conducting surface region and a state of the switching means of making the connection or vice versa.

11 Claims, 2 Drawing Sheets

IMPLANTABLE LEAD WITH SELECTIVELY OPERABLE ELECTRODES

BACKGROUND OF THE INVENTION

The invention concerns an implantable electrode arrangement which includes an electrode lead with a plurality of electrically conducting surface regions in the region of the distal end for outputting electrical signals to a heart and/or for receiving signals from a heart. The output and/or received signals can be connected by way of at least one electric line of the electrode lead to a cardioelectric device for a defibrillator or cardiac pacemaker where the cardioelectric where the cardioelectric device receives electrical signals and/or outputs pulses.

Electrode arrangements with an electrode line and a plurality of electrically conducting surface regions for example of tip or ring electrodes at the distal end of the electrode line are known for example from EP 0 571 797, U.S. Pat. No. 4,848,352 and U.S. Pat. No. 4,628,934. In the known electrode arrangements the electrically conducting surface portions which serve as stimulation or sensing electrodes are individually connected to a cardiac pacemaker or defibrillator by means of electric lines which extend in the electrode line. Each of the above-mentioned publications also describes selecting from the plurality of electrodes or electrode combinations, the respectively most suitable ones thereof in order to use them for example for stimulation of a human heart. A disadvantage with the known electrode arrangements is that they can usually only be employed together with specifically adapted cardiac pacemakers or defibrillators which make it possible at the proximal end of the electrode line to contact all feed lines which lead to the electrically conducting surface regions.

Conventional electrode arrangements are those in which only one or two electrical conductors extend in the electrode line, depending on whether the electrode arrangement is intended for unipolar or bipolar stimulation.

Electrode lines with a single-wire connection between the proximal end of the electrode line and the electrically conducting surface regions at the distal end of the electrode line are suitable for unipolar stimulation in which stimulation pulses are outputted between the electrically conducting surface regions at the distal end of the electrode line and a neutral electrode such as for example a casing of a cardiac pacemaker. Also known moreover is bipolar stimulation in which the stimulation energy is outputted between various ones of the electrically conducting surface regions at the distal end of the electrode line. For bipolar stimulation, the electrode line has a two-wire connection between the proximal and distal ends, such connection being made by way of two separate electric lines.

SUMMARY OF THE INVENTION

The object of the invention is to also make available the advantages of electrode arrangements having a plurality of electrically conducting and individually operable surface regions, for cardiac pacemakers or defibrillators having conventional one-wire or two-wire connections.

According to the invention that object is attained by an electrode arrangement of the kind set forth in the opening part of this specification, which is distinguished by switching means that are arranged in the electrode lead or line and are connected to the electric line and at least one electrically conducting surface region such that they can make or break a connection between the electrically conducting surface region and the cardioelectric device in the region of the electrode lead, and by control means that are arranged in the electrode lead and are connected to the electric line for receiving control signals and to the switching means for switching over from a state of the switching means of breaking the connection between the electric line and the electrically conducting surface region and a state of the switching means of making the connection and vice versa.

An electrode arrangement of that kind can conventionally be in the form of a single-wire or two-wire line with the usual electrical connections for a cardiac pacemaker or defibrillator. The control signals for the control means for switching the connection between individual electrically conducting surface regions and the cardiac pacemaker or defibrillator are put by the defibrillator, for example, in the form of digital signals onto the at least one electric line in the electrode lead and are thus passed to the control means. The control means decode each received control signal and correspondingly switch on or off individually or in groups connections between the electric line and the electrically conducting surface regions.

An electrode arrangement of that kind needs in the minimum situation only a single electrical conductor which goes from the proximal end of the electrode line to the switching means and the electrically conducting surface regions at the distal end of the electrode line. The reference potential for the control signals can then be produced for example by way of a neutral electrode with the casing of the pacemaker and can be available by way of the electrically conducting surface regions for the control means.

Preferably the switching means are of such a configuration and arrangement that, by way of the switching means, the connection can be made or broken individually or in groups between a plurality of and all electrically conducting surface regions and electric lines. That can be effected for example by a switching element being provided for each electrically conducting surface region. An electrode arrangement of that kind makes it possible to switch all possible combinations of electrodes.

Preferably, the control means are actuatable by control signals by way of the electric line in such a way that the connection can be made or broken individually or in groups between a plurality of or all electrically conducting surface regions and the electric line. For that purpose the control means include a decoder which for example can decode digital signals for switching the electrode connections on and off and can convert corresponding switching-on or switching-off signals for the switching means. For an electrode line with eight electrodes it is possible to use for example 8-bit control signals in which one bit is always precisely associated with an electrode and the value of the bit—1 or 0—corresponds to the required switching state of the corresponding switching means—on or off—. In this respect the digital control signals are so selected that they can be clearly identified, for example by virtue of their edge gradient, as control signals, even if they have superimposed thereon cardiac signals or voltage pulses for output to the heart. For that purpose the control means preferably have suitable filters which are so designed that they transmit only control signals to a decoder of the control means and retain further signals which are superimposed on the control signals.

In order to prevent damage to the control means for the stimulation pulses, there are preferably provided switch-off means which respond to stimulation pulses applied to the electric line and during the application of such pulses interrupt the connection between the control means and the electric line.

Preferably there is also provided an energy storage means which for the supply of energy for the switching and/or control means is connected thereto and can be charged up by way of the electric line. In that case the energy storage means is preferably a capacitor. The capacitor can be constantly charged with a low level of power by way of an electric one-wire or two-wire line of the electrode line and if required can also make available to the control or switching means higher levels of energy than is available by way of the electric line. In that case of a one-wire line the capacitor is charged by way of that one-wire line and one of the electrically conducting surface regions and a casing, which serves as a neutral electrode, of a cardiac pacemaker.

The switching means are preferably power field effect transistors. Practically no power is required for switching transistors of that kind. In addition in the conducting state such transistors have only a low level of ohmic resistance.

The control means preferably include electrically erasable or programmable read only memories, referred to as EEPROMs. In that way the control means can be easily programmed, that is to say it is easily possible to determine what kind of control signals produce which switching state in terms of the connection between the individual electrically conducting surface regions and the electrode line.

A cardiac pacemaker or defibrillator, for operation of an electrode arrangement of that kind, does not require any further components, apart from a signal generator for the control signals for the control means of the electrode arrangement. A signal generator of that kind preferably includes a storage means for preferred electrode combinations and the corresponding control signals.

BRIEF DESCRIPTION OF THE DRAWINGS

The invention will now be described in greater detail by means of embodiments with reference to the accompanying drawings in which.

DETAILED DESCRIPTION OF THE INVENTION

Figure 1:
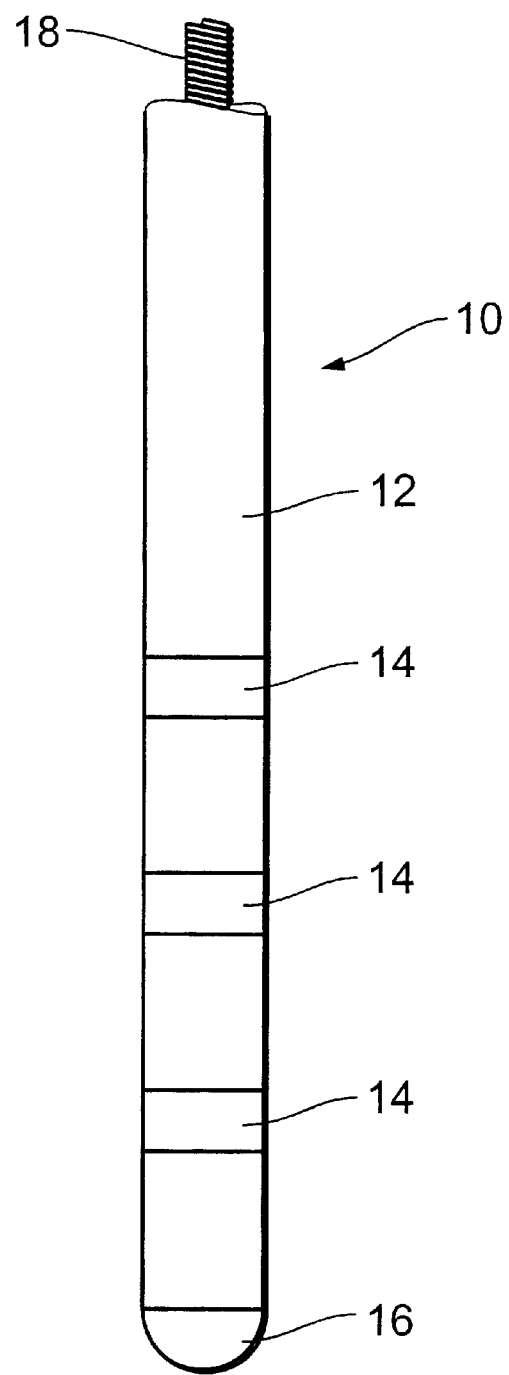
FIG. 1 shows the distal end of an electrode line with electrically conducting surface regions as electrodes.

The distal end shown in FIG. 1 includes an electrode lead 10 with an insulating case 12 and ring electrodes 14 disposed thereon, as well as a tip electrode 16 at the outermost end of the electrode lead 10. A coiled electric line 18 extends in the interior of the electrode lead 10 and serves for the transmission of electrical signals from and to the electrodes 14 and 16. The electrodes 14 and 16 can include, for example, metal. The essential consideration is that the electrodes 14 and 16 form electrically conducting surface regions of the electrode lead 10, which can be at least partly connected to the electric line 18.

Figure 2:
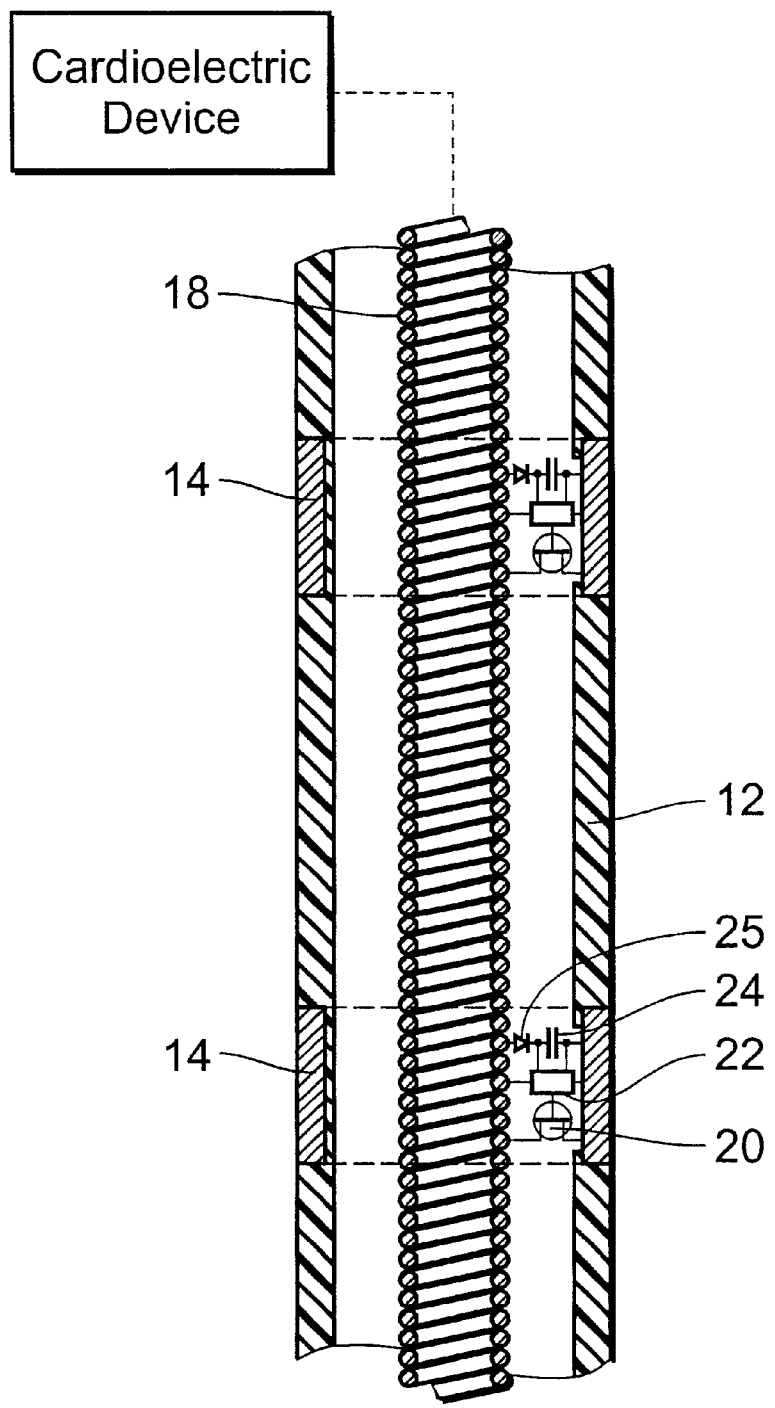
FIG. 2 is a view in longitudinal section through a part of the electrode line shown in FIG. 1.

The structure of the electrode lead 10 can be seen from the view in the longitudinal section of FIG. 2 which extends through the electrode lead 10 in the region of two ring electrodes 14. Shown therein is the coiled electric line 18 which extends within the insulating case 12. The following electrical components are disposed between the line 18 and each ring electrode 14 in each case, a field effect transistor 20, a decoder or a control unit 22, and a capacitor 24 with a rectifier diode 25 connected in series therewith. The field effect transistors 20 are power transistors of low forward resistance in the conducting state. They each represent a respective switching means for making or breaking an electrical connection between the electric line 18 and a respective ring electrode 14. The field effect transistors 20 are actuated by the control unit or decoder 22. The control unit or decoder 22 has two control inputs of which one is connected to the electric line 18 and the other to a respective ring electrode 14. By way of the control inputs, the control unit 22 can receive control signals which are outputted, for example, by a cardiac pacemaker by way of the electric line 18 and a neutral electrode such as the cardiac pacemaker casing, and which accordingly are represented as a potential sequence which is between the electric line 18 and a ring electrode 14. In this case the ring electrode 14 is connected to the neutral electrode by way of a body into which it is inserted.

The energy supply for the control unit 22 is afforded by a capacitor 24 which is also arranged between the line 18 and a respective ring electrode 14. The capacitor 24 is supplied with energy by way of the electric line and the diode 25 on the one hand and on the other hand by way of the ring electrode 14 and the neutral electrode (not shown) corresponding thereto, from the cardiac pacemaker, and charged with a high level of ohmic resistance.

By way of suitable control signals, any one of the electrodes 14 and 16 can be connected to or disconnected from the line 18 by means of the control units 22 and the field effect transistors 20.

The control means shown in FIG. 2 include EEPROMs, that is to say electrically erasable and programmable read only memories which are configured by way of suitable control signals and which provide for the desired association of control signals and connections between the electrodes 14 and 16 and the line 18.

Also integrated into the control unit 22 are switch-off means which are responsive to stimulation pulses which occur on the electric line 18 and which interrupt the connection to for example a decoder which is integrated in the control unit 22, during the duration of such stimulation pulses.

What is claimed is:

1. An electrode arrangement comprising:

an insulating case having a distal end and a plurality of electrically conductive surface regions spaced from one another in a line at the distal end;

at least one electric line disposed within the insulating case, said at least one electric line enabling connection of the plurality of electrically conductive surface regions to a cardioelectric device, said plurality of electrically conductive surface regions performing at least one of outputting electrical signals to a heart and receiving electrical signals from a heart;

first and second switching means, arranged at the distal end of the insulating case, for electrically connecting respective electrically conductive surface regions to a respective one of the at least one electric line where the resultant connections to the cardioelectric device can be made or broken by the first and second switching means at the respective electrically surface regions conductive of the insulating case; and control means arranged in the insulating case and connected to the respective one of the at least one electric line and to each respective electrically conductive surface region in order to receive control signals from the respective one of the at least one electric line and a respective electrically conductive surface region, said control means being electrically connected to said first and second switching means where the received control signals cause at least one of the first and second switching means to operate between a state of breaking the connection between the respective one of the at least one electric line and a respective electrically conductive surface region and a state of making the connection between the respective one of the at least one electric line and the respective electrically conductive surface region.

2. The electrode arrangement according to claim 1, wherein the first and second switching means each enable a connection between a respective one of the plurality of electrically conductive surface regions and the respective one of the at least one electric line to be made or broken individually.

3. The electrode arrangement according to claim 1, wherein the first and second switching means enable a connection between a group of the plurality of electrically conductive surface regions and the respective one of the at least one electric line to be made or broken.

4. The electrode arrangement according to claim 1, wherein the control means are actuable by control signals via the respective one of the at least one electric line in such a way that the connection between the plurality of electrically conductive surface regions and the respective one of the at least one electric line can be made or broken between the respective one of the at least one electric line and one of individual electrically conductive surface regions and a group of the electrically conductive surface regions.

5. The electrode arrangement according to claim 1, further comprising an energy storage means for storing and supplying energy, the energy storage means being connected to at least one of the first and second switching means and the control means and being charged up via the at least one electric line.

6. The electrode arrangement according to claim 5, wherein the energy storage means is an electrical capacitor.

7. The electrode arrangement according to claim 1, wherein the first and second switching means include field effect transistors.

8. The electrode arrangement according to claim 1, wherein the control means include electrically erasable and programmable read only memories (EEPROMS).

9. The electrode arrangement according to claim 1, wherein the cardioelectric device is one of a defibrillator and a cardiac pacemaker.

10. The electrode arrangement according to claim 1, wherein the cardioelectric device at least one of receives electrical signals and outputs pulses.

11. An electrode arrangement comprising:

an insulating lead having a distal end, a proximal end, and first and second electrodes spaced from one another at the distal end;

a sole electric line disposed within the insulating lead extending from the distal end to the proximal end of the lead, said sole electric line enabling connection of the first and second electrodes to a cardioelectric device, said first and second electrodes capable of at least one of outputting electrical signals to a heart and receiving electrical signals from a heart;

first switching means, arranged at the distal end of the insulating lead, for electrically connecting said first electrode to the sole electric line;

second switching means, arranged at the distal end of the insulating lead, for electrically connecting said second electrode to the sole electric line where the respective, resultant connections to the cardioelectric device can be made or broken by the first and second switching means; and control means arranged in the insulating lead and connected to the sole electric line and to said first and second electrodes in order to receive control signals from one of the sole electric line, the first electrode, and the second electrode, said control means being electrically connected to said first and second switching means where the received control signals cause the first and second switching means to operate between a state of breaking the connection between the sole electric line and at least one of the first and second electrodes and a state of making the connection between the sole electric line and at least one of the first and second electrodes.

* * * * *